US00PP10853P

United States Patent [19]

Ludeke

[11] Patent Number: Plant 10,853

[45] Date of Patent: Apr. 6, 1999

[54] OAK TREE (*Q. ALBA*×*Q. MICHAUXII*)×*Q. MICHAUXII* NAMED 'SOUTHERN CROSS'

[76] Inventor: Martin Glen Ludeke, 715 Gillespie Ave., Charlottesville, Va. 22902

[21] Appl. No.: 898,196

[22] Filed: Jul. 22, 1997

[51] Int. Cl.[6] ..... A01H 5/00

[52] U.S. Cl. ..... Plt./225

[58] Field of Search ..... Plt./53.7

[56] References Cited

PUBLICATIONS

Little, Elbert L., Checklist of United States Trees, United States Department of Agriculture, Washington, D.C., pp. 224 and 236, 1979.

Palmer, Ernest J., "Hybrid Oaks of North America", Journal of the Arnold Arboretum, vol. XXIX No. 1, pp. 5, 6, 12 and 16, 1948.

Jaynes, Richard A., Nut Tree Culture in North America, Northern Nut Growers Association, Inc., p. 410, 1979.

William Harlow et al., Textbook of Dendrology Covering the Important Forest Trees of the United States and Canada, McGraw–Hill Book Company, New York, New York, p. 318, 1941.

A. M. Winchester, Genetics A Survey of the Principles of Heredity, Houghton Mifflin Company, pp. 436–437, 1966.

W. P. Cottman et al., Oak Hybridization at the University of Utah, pp. 3, 29, and 50, 1971.

*Primary Examiner*—Howard J. Locker
*Assistant Examiner*—Kent L. Bell

[57] ABSTRACT

A new variety of oak is disclosed which is a backcross which has an extremely rapid growth rate, a strong central leader, graceful branching habit and tolerance of wet, periodically flooded soil.

5 Drawing Sheets

The present invention relates to a new and distinct variety of oak tree which has been named the 'Southern Cross'.

Near a swamp east of Richmond, Va. I discovered a group of three oak trees isolated from all others. The group consisted of one *Quercus alba,* one *Quercus michauxii* and an obvious hybrid between the two, referenced as the *Quercus beadlei.* It is estimated that the chances of an oak hybrid are approximately 1 in 100,000. From 1980 to 1988 I collected over 600 acorns from the hybrid and planted the resulting seedlings at the edge of a marsh near Charlottesville, Va. In 1988 the original hybrid was blown down in a storm, thereby eliminating the source of acorns of this species. While many of the offspring showed good, vigorous growth rates, one tree was clearly unique. In a genus where one might expect 30cm (12") of growth per year this particular variety has averaged nearly a meter (3') per year, developing a strong central leader. After 16 years of growth this tree is 14.6 m (48') tall with a spread of 12.2 m (40') in comparison with a standard oak which would be only 12–16 feet. Its form is pyramidal featuring a strong central leader with long narrow branches. The trunk tapers slowly from 25.4 cm (10") in diameter at 1.4 m (4½') high to 10 cm (4") in diameter at 7.6 m (25') high. The branches, 5–7.5 cm (2–3") in diameter at the base, extend 6.1 m (20') from the tree. The lowest branches initially ascend from the trunk at 45° angles then gradually arc downward ranging from 75°–90° relative to the tree. The middle branches remain at 45° and the highest branches assume narrower angles of growth, closer to 30°.

After years on observation and comparison with other trees I am convinced that this oak would be a valuable selection for a number of reasons. Its strong central leader, rapid growth rate and gradual taper make it as valuable as a timber tree. Secondly its rapid growth rate and delicate form make it an ideal specimen tree for the landscape industry. Lastly, its tolerance of wet, marshy soil would make it useful in wetland reparations, taking areas heretofore unusable for cultivating and turning these areas into income producing land without harming or depleting the wildlife.

Asexual propagation of this new variety was performed by myself using scionwood grafted onto a mature *Q. alba.*

Observations of these progeny indicate the characteristics and distinctions of my new variety are established and can be perpetuated in succeeding generations. I am not aware of another oak which combines following traits: rapid growth, good timber form, graceful branching habit and tolerance of wet, periodically flooded soil.

BRIEF DESCRIPTION OF THE DRAWINGS

The accompanying colored photographs illustrate the overall performance and color of the new hybrid Oak tree, showing the colors as true as it is reasonable possible to obtain in colored reproductions of this type. Actual bark and foliage colors may differ from bark and foliage colors in the photograph due to light reflectance.

DETAILED BOTANICAL DESCRIPTION

Figure 1:
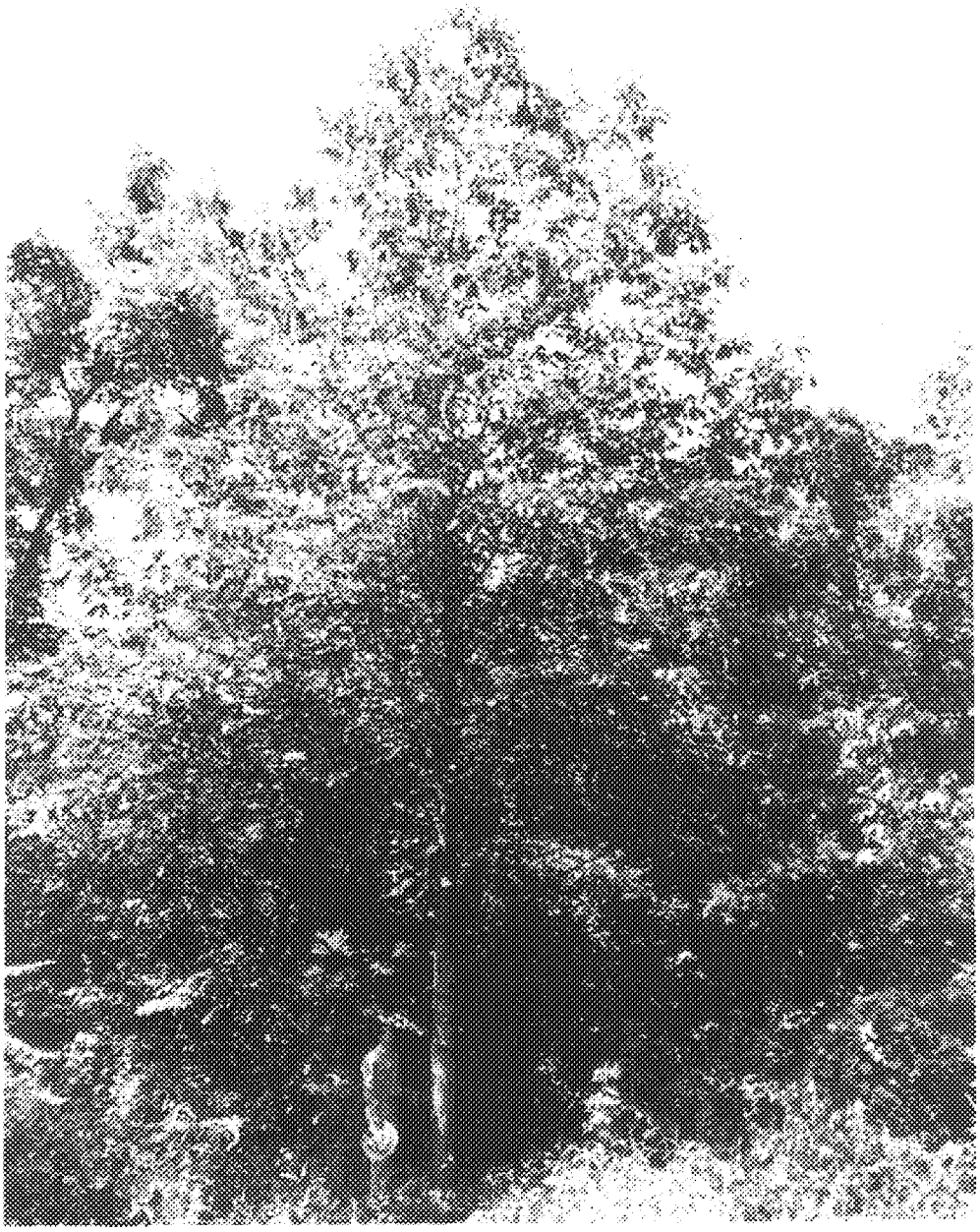
FIG. 1 is a color photograph of my selection in full leaf relative to a 1.8 m (6') man.
Figure 2:
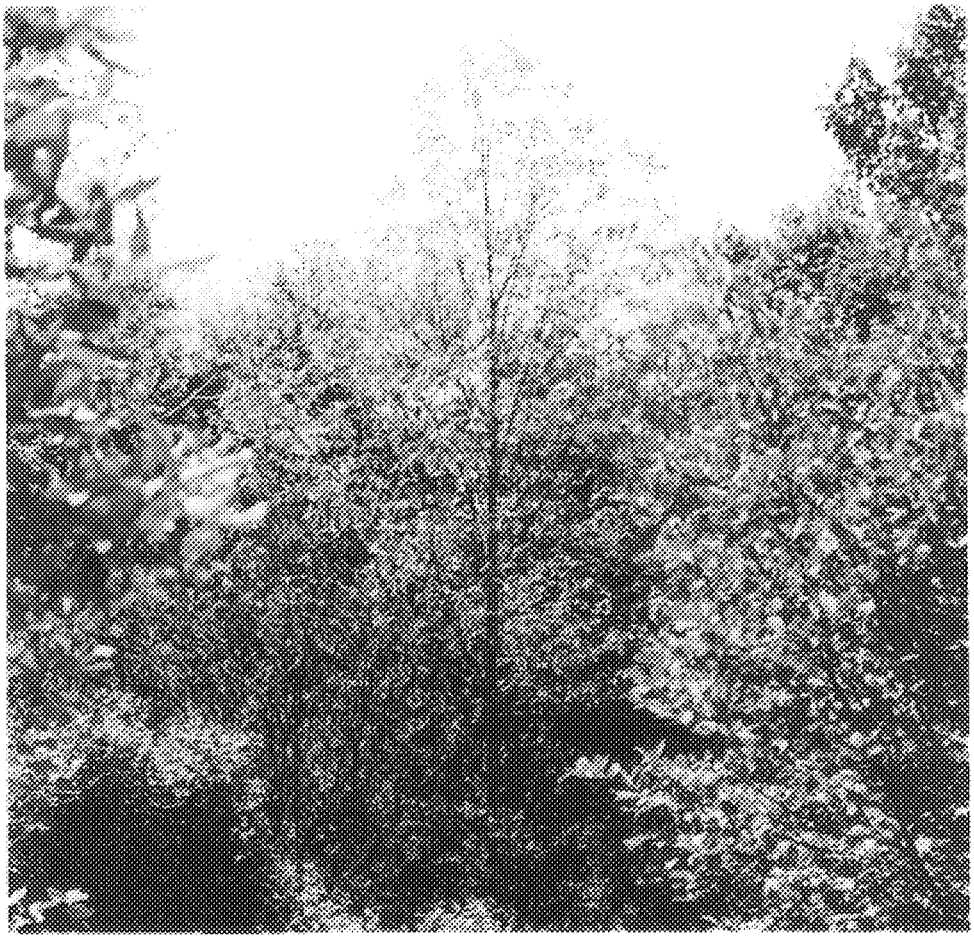
FIG. 2 is a color photograph of my selection, nearly bare of foliage, illustrating its strong central leader.
Figure 3:
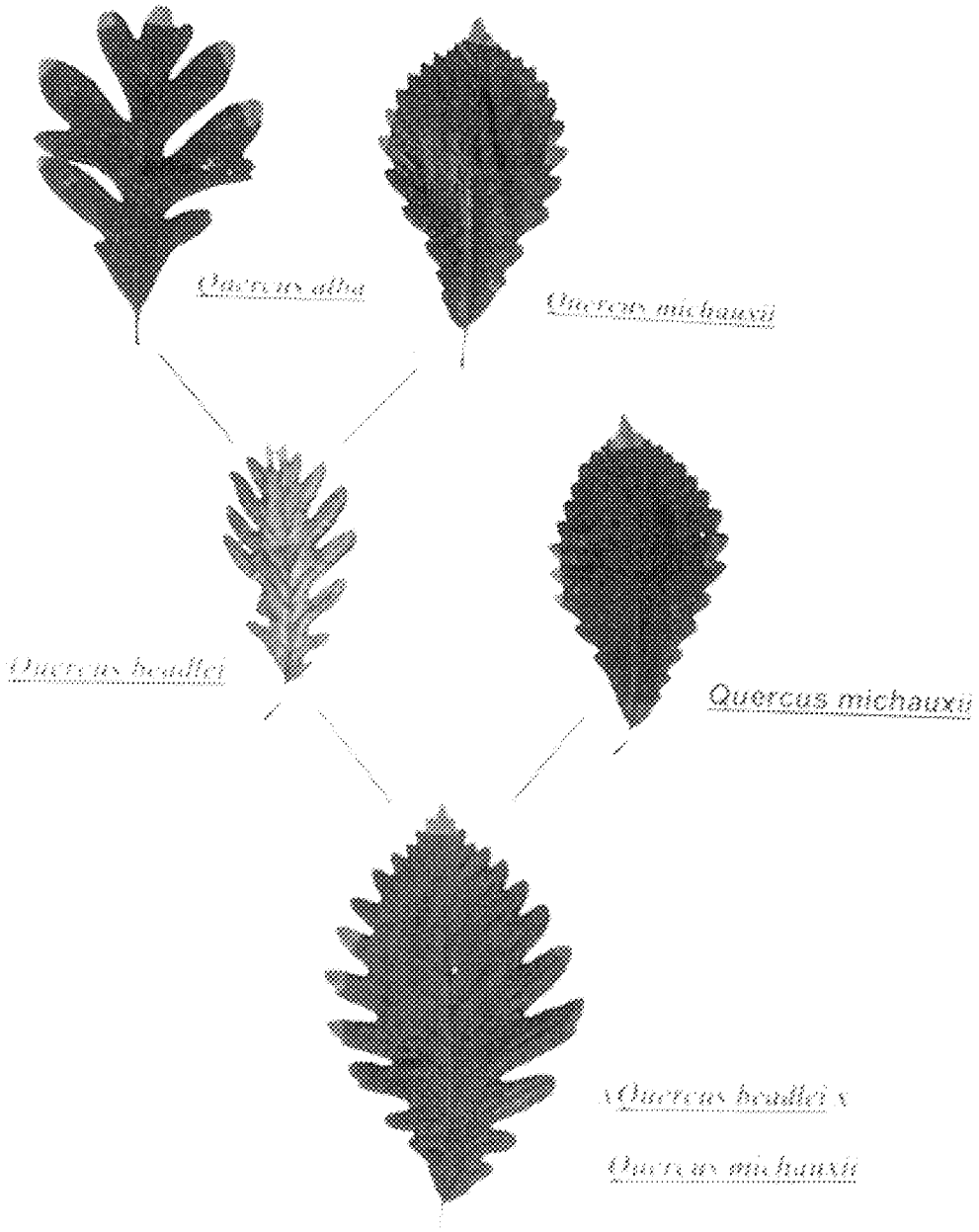
FIG. 3 is a color photograph of oak leaves depicting the hybrid ancestry of my selection.
Figure 4:
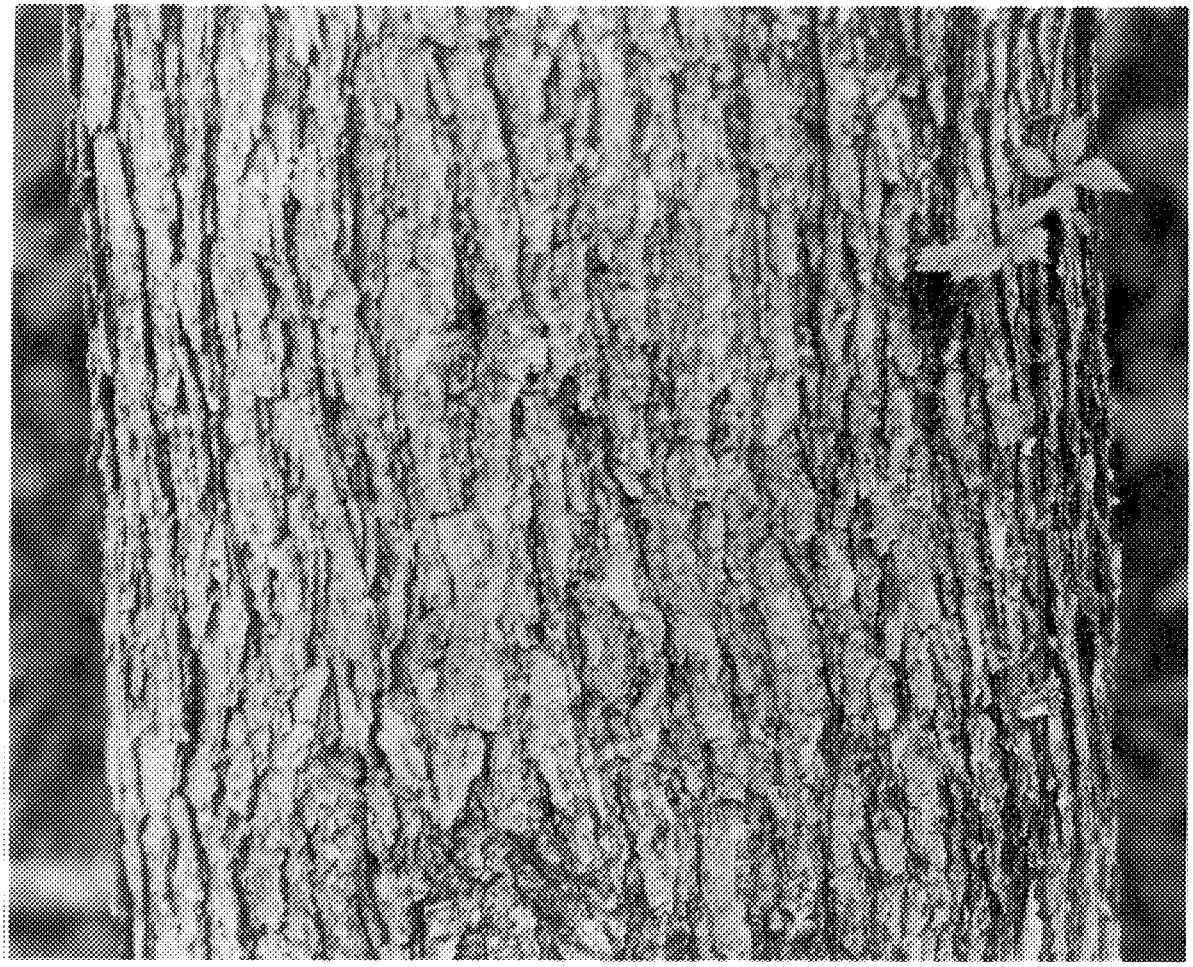
FIG. 4 is a color photograph showing the bark color and texture.
Figure 5:
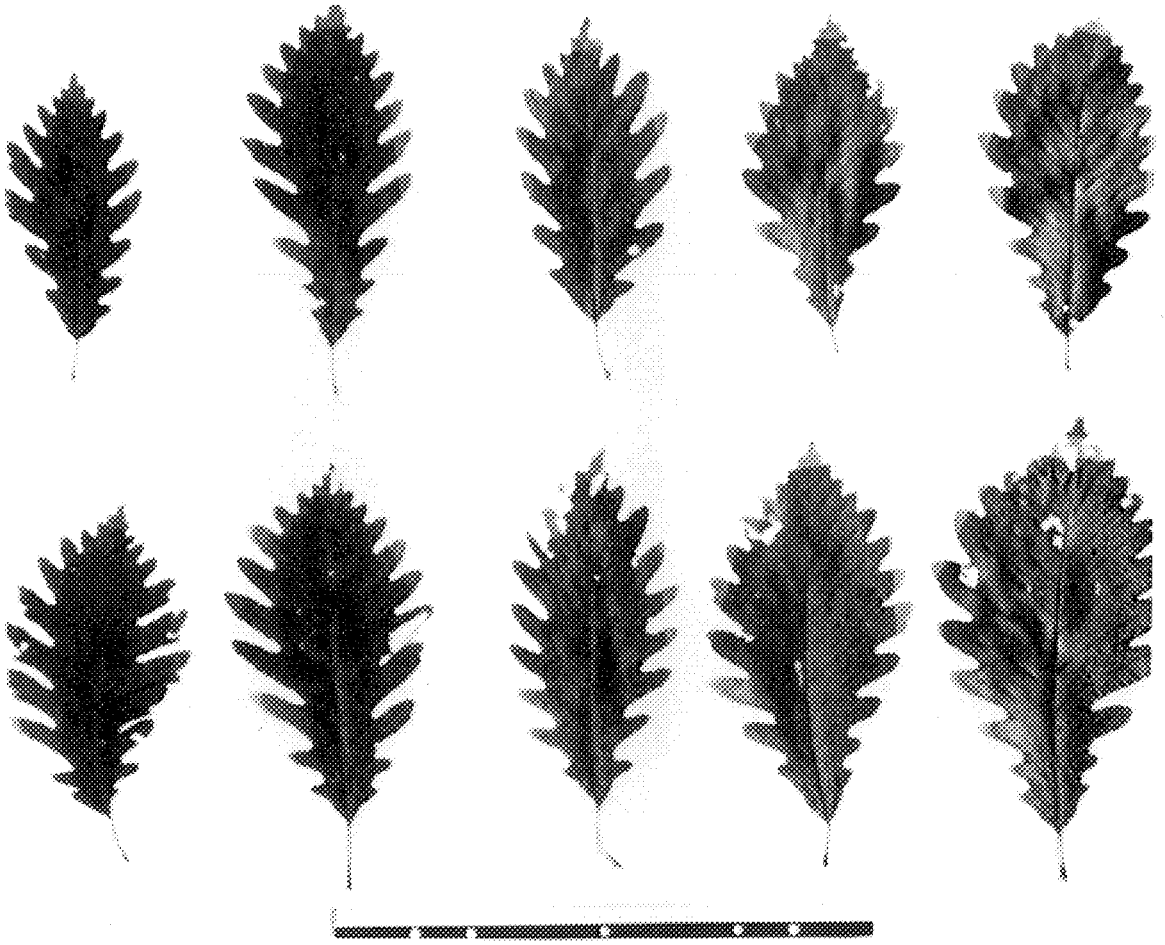
FIG. 5 is a color photograph showing the various leaves taken from the disclosed tree.

The following is a detailed description of the new variety with color terminology based on The Royal Horticultural Society Color Charts (R.H.S.C.C.).

Parentage: Careful analysis of various genetic characteristics suggest my variety is the offspring of a *Q. michauxii* pollen parent and a *Q. beadlei* seed parent. The *Q. beadlei* is a hybrid resulting from a cross between a *Q. alba* and a *Q. michauxii* and is recognized in the Checklist of United States Trees, p. 224. (Little, Elbert L., Forest Service of the U.S. Department of Agriculture, September 1979) As a backcross, the seed was from the *Q. beadlei* and the pollen from a *Q. michauxii,* thereby making the *Q. michauxii* a parent as well as a grand parent. The offspring of an interspecific backcross will strongly resemble one of the original parent species and this selection does reflect a largely *Q. michauxii* ancestry with some *Q. alba* traits in evidence. The following characteristics were used to verify the parentage of the disclosed tree. '*Southern Cross' leaf lobe glands are fully formed with entire margins indicating the Q. michauxii* paternity. This is a trait of *Q. michauxii* and does not exist in *Q. alba.* Leaf lobes are poorly formed with indistinct margins in *Q. beadlei.* The number of leaf lobes in 'Southern Cross' is intermediate between *Q. michauxii* and *Q. beadlei. The depth of the sinuses (in percentage) is intermediate between Q. michauxii* and *Q. beadlei.* The terminal bud, while varying, is closer to *Q. michauxii* than *Q. alba* in size. The terminal bud tip is acute, resembling *Q. michauxii,* and the terminal bud color (grey-orange/ R.H.S.C.C. FAN 4, 166C) is similar to that of the *Q. michauxii.*

In the branching habit of 'Southern Cross' the emerging stems, relative to the trunk, are always initially ascending but through time and gravity can become perpendicular. This is a *Q. michauxii* trait as the *Q. alba* branches are much more variable—initially ascending, perpendicular, or descending.

The bark structure in 'Southern Cross' resembles *Q. michauxii,* having narrower ridges and smaller scales than *Q. alba.* Only very old *Q. alba* trees tend to have bark in narrow ridges. The dried wood of 'Southern Cross' also fractures into splints with relative ease, a known trait of the *Q. michauxii.*

The tree shape is pyramidal featuring a strong central leader, a crown spread of 12.2 m (40') and a height of 14.6 m (48'). Narrow branches, with basal diameters of 5–7.5 cm (2–3"), and lengths of 6.1 m (20'), diverge from the trunk at 45° angles. The ascent of the lowest branches rapidly broadens to 60° and 3.1 m (10') from the trunk can vary from 75°–90°. The middle branches remain at 45° angles while the highest branches assume narrower angles, closer to 30°.

The outer surface of the bark is gray-green (R.H.S.C.C. FAN4, 179B) irregularly furrowed or scaly with the inner surface being brown (R.H.S.C.C. FAN4, 200B).

New twig growth is covered with a pale, caducous pubescence which largely sloughs off by midsummer but can be detected into autumn in less exposed areas (i.e. near axial buds and petiole attachments). Twigs are moderately stout with varying colors relative to the amount of sunlight received. New growth in full sun is yellow-green (R.H.S.C.C. FAN 3, 146B) while shaded new growth is grey-green (R.H.S.C.C. FAN 4 197A). Second year growth in full sun is grey-green (R.H.S.C.C. FAN 4, 195A). Two year old stems in shade are yellow-green (R.H.S.C.C. FAN 3, 152A) on the upper side and grey-green (R.H.S.C.C. FAN 4, 197A) on the lower side.

Mature, one-year-old twigs are smooth and older stems remain smooth until they reach a diameter of 1.9–3.0cm (¾–1¼"). At that time, fissures begin to appear in the bark on the upper side of the stem. As the branch thickens fissures form on the sides and by the time the diameter has reached 3.8–5cm (1½"–2") the entire branch is scaly and furrowed, similar in texture and color (outer surface grey-green R.H.S.C.C. FAN 4, 197B/inner surface: brown-R.H.S.C.C. FAN 4 200B) to the trunk. Terminal buds are 0.5–0.6cm (3/16–¼") long, acute with grey-orange (R.M.S.C.C. FAN 4, 166C) puberlous scales, pale on the margin.

Leaves are 17.5–25.4cm (7–10") long and 10–12.5cm (4–5½") wide, oblong to obovate in form. The leaf tip is acute and the base is cuneate. The margin is evenly toothed or nearly so having 8–14 pairs of glandular tipped lobes with shallow to moderately deep sinuses (extending ¼ to ½ the distance to the midrib depending on the amount of light received). Fall color is grey-orange (R.H.S.C.C. FAN 4, 177B). The upper surface is yellow-green (R.H.S.C.C. FAN3, 146A) and lustrous, the lower surface a lighter yellow-green (R.H.S.C.C. FAN3, 148C) and pubescent. Petioles are stout, varying from 1.6–2.5 cm (⅝–1") in length and frequently curved.

Staminate and pistillate flowers are seen on the tree in the late spring but to date no mature fruit has been observed. The growth rate is fast, averaging nearly 0.9 m (3') per year.

'Southern Cross' has demonstrated a high resistance to natural pests with less than about 5% of the overall foliage being affected. The hybrid further has displayed an extremely high resistance to oak wilt, galls, powdery mildew and fungus.

I claim:

1. A new and distinct variety of oak tree, a backcross between *Q. michauxii* and the hybrid *Q. beadlei,* substantially as herein shown and described, characterized particularly as to novelty by the unique combination of a rapid growth rate, a good timber form, a graceful branching habit and a tolerance of wet, periodically flooded soil.

* * * * *